United States Patent [19]
Baniel et al.

[11] Patent Number: 5,426,220
[45] Date of Patent: Jun. 20, 1995

[54] CITRIC ACID EXTRACTION

[75] Inventors: Avraham M. Baniel, Jerusalem; Aharon M. Eyal, Kibbutz Ramat Rachel, both of Israel

[73] Assignee: Innova, S.A., Luxembourg, Luxembourg

[21] Appl. No.: 271,248

[22] Filed: Jul. 7, 1994

Related U.S. Application Data

[63] Continuation of Ser. No. 26,410, Mar. 4, 1993, abandoned.

[51] Int. Cl.$^6$ .................. C07C 51/42; C07C 51/48
[52] U.S. Cl. .................................................. 562/580
[58] Field of Search ................................... 562/580

[56] References Cited

U.S. PATENT DOCUMENTS

| | | | |
|---|---|---|---|
| 3,944,606 | 3/1976 | Rieger et al. | 260/535 |
| 4,275,234 | 6/1981 | Baniel et al. | 562/584 |
| 4,334,095 | 6/1982 | Baniel | 562/584 |
| 4,720,577 | 1/1988 | Wojtech et al. | 562/580 |
| 4,994,609 | 2/1991 | Baniel et al. | 562/580 |
| 5,231,225 | 7/1993 | Baniel et al. | 562/513 |

FOREIGN PATENT DOCUMENTS

| | | | |
|---|---|---|---|
| 0423610 | 6/1991 | European Pat. Off. | 562/580 |
| 0432610 | 6/1991 | European Pat. Off. | |

*Primary Examiner*—José G. Dees
*Assistant Examiner*—Barbara S. Frazier
*Attorney, Agent, or Firm*—Foley & Lardner

[57] ABSTRACT

In the production of citric acid aqueous mother liquor originating from a lime/sulfuric acid process is subjected to a multi-stage counter-current extraction with an amine based organic extractant. A solution of a further amount of citric acid derived from direct extraction of a citric acid fermentation broth is judiciously injected into the organic phase stream in the counter-current extraction and a combined extract is withdrawn from the operation. This extract can be subjected to any known treatment for the recovery of citric acid values.

9 Claims, No Drawings

CITRIC ACID EXTRACTION

This application is a continuation of application Ser. No. 08/026,410, filed Mar. 4, 1993, now abandoned.

FIELD OF THE INVENTION

The present invention is in the field of citric acid production and is directed to an improvement in the process of solvent extraction of citric acid from an aqueous solution by means of a water-immiscible organic extractant in a multi-stage counter-current extraction operation.

BACKGROUND OF THE INVENTION

Citric acid is produced commercially by fermentation of carbohydrates. By one known method, essentially clean carbohydrates such as glucose or refined sucrose are used for the fermentation and this yields a relatively clean fermentation broth from which citric acid can be recovered by direct extraction with a water-immiscible organic extractant followed by water stripping of the resulting extract as described, for example, in U.S. Pat. Nos. 3,944,606, 4,275,234 and 4,334,095. According to U.S. Pat. No. 3,944,606 alkali metal or ammonium citrates are produced directly from a fermentation broth by extraction with a water-immiscible organic extractant consisting of a mixture of a secondary or tertiary amine with an organic solvent, and the resulting organic extract is re-extracted with a compound that forms an alkali metal or ammonium salt of citric acid.

According to U.S. Pat. No. 4,275,234 a citric acid fermentation broth is extracted with a water-immiscible organic extractant which comprises a solution of at least one secondary or tertiary amine in which the aggregate number of carbon atoms is at least 20 in admixture with hydrocarbon and alcohol and the resulting extract is stripped with water at a temperature which is higher, preferably by at least 20° C. than the broth extraction temperature.

According to U.S. Pat. No. 4,344,095 a citric acid fermentation broth is extracted with a mixture of a water-immiscible amine and a water-immiscible organic acid dissolved in a suitable water-immiscible solvent, and the resulting extract is back-extracted with water.

The most common source of carbohydrate for citric acid fermentation is beet molasses. Citric acid fermentation on such a nutrient yields a fermentation broth rich in cations and the yield of direct extraction thereof is poor. Accordingly, the recovery of citric acid from such broth is usually by way of the so-called "lime/sulfuric acid process". This process comprises a so-called "liming" operation, i.e. treatment of the fermentation broth with calcium hydroxide to yield calcium citrate which is filtered off, washed and decomposed with aqueous sulfuric acid. The calcium sulfate that forms is filtered off and the resulting aqueous acidic solution is gradually evaporated in a crystallizer whereupon citric acid crystallizes leaving behind a saturated mother liquor which holds significant residual amounts of citric acid together with accumulated impurities. This mother liquor will be referred to hereinafter as "lime sulfuric acid/citric acid mother liquor".

From the lime sulfuric acid/citric acid mother liquor the residual amounts of citric acid cannot be recovered by crystallization because this would inevitably lead to the inclusion of impurities in the crystallizing citric acid. Accordingly, residual amounts of citric acid are recovered from a lime sulfuric acid/citric acid mother liquor by multi-stage counter-current water extraction with a water-immiscible extractant, for example in the manner disclosed in EP 0432610 using as extractant a mixture of at least one organic amine and a liquid hydrocarbon.

From the extraction of a sulfuric acid/citric acid mother liquor with an organic extractant, there results an organic extract whose degree of purity is similar to that of an extract obtained by direct extraction of a fermentation broth, e.g. in accordance with the teachings of any of U.S. Pat. Nos. 3,944,606, 4,275,234 and 4,334,095. It would therefore be of advantage if such extracts could be combined for the purpose of the recovery of citric acid values therefrom either in the form of free acid or as alkali metal or ammonium citrates. However, simple combination of such organic citric acid extracts is impractical because of the different concentrations thereof, the extract resulting from the multi-stage counter-current extraction of a lime sulfuric acid/citric acid mother liquor being as a rule more concentrated than the extract obtained from direct organic solvent extraction of a fermentation broth. Accordingly, a mere combination of the final extracts would result in dilution which is disadvantageous for the recovery of citric acid values.

It is the object of the present invention to provide a process by which a first organic extraction citric acid extract obtained by multi-stage counter-current extraction of a lime sulfuric acid/citric acid mother liquor and a second organic extractant citric acid extract obtained by direct extraction of a fermentation broth can be combined to yield as product an organic extractant solution of citric acid of the same concentration as that which would be obtained by extraction of the lime sulfuric acid/citric acid mother liquor without the addition of any second organic citric acid extract.

SUMMARY OF THE INVENTION

In accordance with the present invention, it has been found that in a multi-stage counter-current extraction of an aqueous citric acid solution with an amine based extractant, it is possible to inject into the operation without disruption of the counter-current extraction operation further amounts of a citric acid solution in an amine based extractant and to obtain as product an extract of similar concentration as would have been obtained without such injection, provided that certain conditions are observed.

On the basis of these findings the invention provides in the manufacture of citric acid, a process that comprises extraction of an aqueous citric acid feed solution derived from a first source of citric acid with a water-immiscible amine based extractant that includes at least one organic amine and at least one liquid hydrocarbon, in which process aqueous and organic phases are contacted counter-currently in a multi-stage extraction operation to produce a first stream of an organic citric acid extract; and injection into the organic phase of a second stream of an organic citric acid extract in the same amine based extractant and derived from a second source of citric acid, the improvement by which:

(i) said aqueous feed solution is a concentrated solution holding citric acid in an amount of at least 40% w/w;

(ii) the concentration of the citric acid in said second stream of organic citric acid extract is less than 1 mol. citric acid per mol. of amine;

(iii) said second stream of organic citric acid extract is injected into said first stream of organic citric acid extract at an intermediary operational phase of the multi-stage extraction operation at which the citric acid concentration in both extracts is essentially the same; and (iv) a product extract is withdrawn from said multi-stage extraction operation.

The product extract withdrawn from the multi-stage extraction operation may be subjected to any known treatment for the recovery of citric acid values therefrom, e.g. in accordance with any of U.S. Pat. Nos. 3,944,606, 4,275,234 and 4,334,095.

The multi-stage counter-current extraction operation of the present invention can be performed either batchwise or continuously.

The organic amine in an extractant used in accordance with the present invention is preferably tertiary with the aggregate number of carbon atoms being at least 18 and preferably from 24–42. Examples of such preferred amines are tricaprylyl and tridodecyl amines.

The extractant used in accordance with the present invention may, if desired, further comprise an alkanol with at least 6 carbon atoms, such as, for example, octanol. Preferably, the amount of alkanol added to the extractant is less than 15% w/w of the total extractant.

Typically, the extraction operation of the present invention is effected with mixer settler batteries with those mixer settler units which, with regard to the flow of the first stream of the organic citric acid extract are downstream of the point of injection of the second organic citric acid extract having a larger capacity than those upstream.

In the performance of the process according to the invention the aqueous citric acid feed may be a lime/sulfuric acid citric acid mother liquor derived from a citric acid fermentation broth by a sequence of operations comprising treating said fermentation broth with calcium hydroxide, separating the so-formed calcium citrate, decomposing the calcium citrate with aqueous sulfuric acid to produce calcium sulfate in an aqueous citric acid solution, separating said aqueous citric acid solution, crystallizing citric acid therefrom by gradual evaporation of water and separating the precipitated citric acid from its mother liquor.

The second stream of an organic citric acid extract which in accordance with the invention is injected into the organic phase may be derived from a direct extraction of a citric acid fermentation broth.

DESCRIPTION OF SPECIFIC EMBODIMENTS

For better understanding the invention will now be described by some specific working examples to which it is not limited.

REFERENCE EXAMPLE A

Fermentation of molasses produced a 20% citric acid fermentation liquor. 4.9 kg of this liquor were mixed after filtration with 320 gr of 60% citric acid mother liquor from the crystallizer. This mixture was reacted with 680 gr of $Ca(OH)_2$ to precipitate calcium citrate. The latter was filtered, washed and reacted with 920 gr of 98% sulfuric acid to form gypsum and a solution of citric acid. The citric acid solution obtained on gypsum filtration was fed to a crystallizer. 1050 gr of crystalline citric acid monohydrate were formed as well as 320 gr of 60% citric acid mother liquor.

REFERENCE EXAMPLE B 320 gr of 60% citric acid mother liquor were counter-currently extracted at 50° C. with 860 gr extractant comprising 56% (1.07 mol/kg) Alamine 304 (tridodecyl lauryl amine produced by Henkel) and 6% octanol in aromatics free kerosene. 4 stages resulted in a raffinate containing most of the impurities and substantially free of citric acid values and an extract of 18.0% citric acid (citric acid to amine molar ratio of 1.09).

EXAMPLE 1

320 gr of 60% citric acid mother liquor obtained as in Reference Example A were counter-currently extracted at 50° C. by an extractant composed similarly to that in Reference Example B. The extractant amount was 230 gr and the number of counter-current stages was seven. 2.23 kg of an extract containing 1.5 mols of citric acid (0.73 mol citric acid per mol of amine) were injected to the organic phase after the third stage. The loaded extractant product of the total operation (extract) contained 2.5 mols of citric acid at concentration of 18.0%, similar to that in Reference Example B. Thus a relatively dilute extract containing 1.5 mols of citric acid was added to the first without leading to dilution of the organic product.

EXAMPLE 2

Fermentation using pure carbohydrates produced fermentation liquor containing 17% citric acid.

575 gr/min of this liquor were extracted after filtration by 740 gr/min of extractant comprising of 56% alamine 304 in aromatics free kerosene. 5 counter-current stages at 50° C. resulted in substantially complete extraction of the acid and in an organic extract containing 11.5% citric acid (0.63 mol citric acid per mol of amine).

EXAMPLE 3

160 gr/min of 60% citric acid mother liquor obtained as in Reference Example A were counter-currently extracted at 50° C. by 120 gr/min of extractant composed similarly to that in Example 2. The number of counter-current stages was 8 after 4 of which the relatively dilute extract obtained in Example 2 was injected. The organic product of the extraction contained 192 gr citric acid per min in concentration of 18.0% similar to that in Reference Example B.

This organic product was counter-currently back-extracted by 195 gr/min of water at 50° C. Four counter-current stages resulted in a 33% aqueous solution.

The organic product of the back-extraction was counter-currently contacted with 150 gr/min of 40% NaOH. 2 stages resulted in 131 gr/min tri-sodium citrate and 860 gr of regenerated extractant free of citric acid.

We claim:

1. In a lime/sulfuric acid process for the manufacture of citric acid, which includes the step of extracting a concentrated aqueous citric acid mother liquor feed solution with a water-immiscible amine based extractant that includes at least one organic amine and at least one liquid hydrocarbon, in which step the aqueous feed and the organic extractant are contacted counter-currently in a multi-stage extraction operation to produce a product organic citric acid extract having a specific final citric acid concentration, the improvement wherein said concentrated aqueous citric acid mother liquor feed solution holds citric acid in an amount of at least 40% w/w; and wherein said process further comprises injecting into the organic phase, during said multi-stage counter-current extraction, a second stream of an organic citric acid extract in the same amine based extractant and derived from direct extraction of a citric acid fermentation broth, the initial concentration of the citric acid in said second stream of organic citric acid extract being less than 1 mol citric acid per mol of amine; wherein said second stream of organic citric acid extract is injected into said first stream of organic citric acid extract at an intermediary operational phase of the multi-stage extraction operation at which the citric acid concentration in both organic extracts is substantially the same; whereby the product organic citric acid extract withdrawn from said multi-stage extraction operation has substantially the same final concentration as said specific final citric acid concentration.

2. A process according to claim 1, wherein said concentrated aqueous citric acid mother liquor feed solution has a citric acid concentration of about 60% w/w.

3. A process according to claim 1, wherein said concentrated aqueous citric acid mother liquor feed solution is derived from a citric acid fermentation broth by a sequence of operations comprising treating said fermentation broth with calcium hydroxide, separating the so-formed calcium citrate, decomposing the separated calcium citrate aqueous sulfuric acid to produce calcium sulfate in an aqueous citric acid solution, separating said aqueous citric acid solution, crystallizing citric acid therefrom by gradual evaporation of water and separating the precipitated citric acid from its mother liquor.

4. A process according to claim 1, which is carried out continuously.

5. A process according to claim 1, wherein said at least one organic amine is a tertiary amine.

6. A process according to claim 5, wherein said tertiary amine is tridodecyl amine, tricaprylyl amine or a mixture thereof.

7. A process according to claim 5, wherein said extractant further comprises a saturated alkanol having at least 6 carbon atoms.

8. A process according to claim 7, wherein the amount of said alkanol is less than 15% w/w of the total extractant.

9. A process according to claim 7, wherein said alkanol is octanol.

* * * * *